(12) United States Patent
Chakrabarti et al.

(10) Patent No.: US 10,655,185 B2
(45) Date of Patent: May 19, 2020

(54) METHODS FOR DIAGNOSIS AND PROGNOSIS OF EPITHELIAL TUMORS

(71) Applicants: H. Lee Moffitt Cancer Center and Research Institute, Inc., Tampa, FL (US); University of Central Florida Research Foundation, Inc., Orlando, FL (US)

(72) Inventors: Ratna Chakrabarti, Winter Springs, FL (US); Richard Ottman, Orlando, FL (US); Domenico Coppola, Tampa, FL (US); Nupam Mahajan, Tampa, FL (US)

(73) Assignees: H. Lee Moffitt Cancer Center and Research Institute, Inc., Tampa, FL (US); University of Center Florida Research Foundation, Inc., Orlando, FL (US)

( * ) Notice: Subject to any disclaimer, the term of this patent is extended or adjusted under 35 U.S.C. 154(b) by 280 days.

(21) Appl. No.: 15/525,787

(22) PCT Filed: Nov. 10, 2015

(86) PCT No.: PCT/US2015/059853
§ 371 (c)(1),
(2) Date: May 10, 2017

(87) PCT Pub. No.: WO2016/077285
PCT Pub. Date: May 19, 2016

(65) Prior Publication Data
US 2017/0335403 A1    Nov. 23, 2017

Related U.S. Application Data

(60) Provisional application No. 62/077,859, filed on Nov. 10, 2014, provisional application No. 62/093,224, filed on Dec. 17, 2014.

(51) Int. Cl.
*G01N 33/574* (2006.01)
*C12Q 1/6886* (2018.01)

(52) U.S. Cl.
CPC ...... *C12Q 1/6886* (2013.01); *C12Q 2600/106* (2013.01); *C12Q 2600/112* (2013.01); *C12Q 2600/118* (2013.01); *C12Q 2600/158* (2013.01)

(58) Field of Classification Search
CPC .................................................. C12Q 1/6886
See application file for complete search history.

(56) References Cited

U.S. PATENT DOCUMENTS

2011/0183866 A1    7/2011  Clarke et al.

OTHER PUBLICATIONS

Fizazi et al, Anticancer Res, 24:2897-2904, 2004.*
Liu et al., "Epstein-Barr Virus-Encoded LMP1 Interacts with FGD4 to Activate Cdc42 and Thereby Promote Migration of Nasopharyngeal Carcinoma Cells," PLoS Pathog, vol. 8, No. 5, e1002690; May 10, 2012.
Ottman et al., Association of miR-17-92 Cluster and its Target, Frabin, with Development of Aggressive Prostate Cancer, Cancer Research, Oct. 1, 2014, vol. 74, p. 5221; Abstract.
International Search Report and Written Opinion issued in corresponding application No. PCT/US2015/059853, dated Feb. 5, 2016, 6 pgs.
Jiang et al. 2005. "Using an AMACR (P504S)/34βE12/p63 cocktail for the detection of small focal prostate carcinoma in needle biopsy specimens". Am J Clin Pathol 123: 231-236. abstract.
Ottman, et al., 2014. MicroRNA expressions associated with progression of prostate cancer cells to antiandrogen therapy resistance. Molecular Cancer 2014, 13:1.

* cited by examiner

*Primary Examiner* — Mark Halvorson
(74) *Attorney, Agent, or Firm* — Meunier Carlin & Curfman LLC

(57) ABSTRACT

A biomarker is disclosed that can distinguish aggressive epithelial tumors in a tissue biopsy from, for example, normal, hyperplastic, and benign neoplastic tumors. The biomarker can also identify epithelial tumors that have become resistant to hormone therapy. Therefore, methods are disclosed for providing diagnosis and prognosis of a subject having, or suspected of having, an epithelial tumor, such as a prostate tumor.

8 Claims, 19 Drawing Sheets

METHODS FOR DIAGNOSIS AND PROGNOSIS OF EPITHELIAL TUMORS

CROSS-REFERENCE TO RELATED APPLICATIONS

This application claims benefit of U.S. Provisional Application No. 62/077,859, filed Nov. 10, 2014, and Application Ser. No. 62/093,224, filed Dec. 17, 2014, which are hereby incorporated herein by reference in their entirety.

STATEMENT REGARDING FEDERALLY SPONSORED RESEARCH

This invention was made with Government Support under Grant No. W81XWH-11-1-0563 from the US Army Medical Research Acquisition Activity. The Government has certain rights in the invention.

BACKGROUND

Androgen blockade therapy has become the mainstay for advanced prostate cancer. However, prolonged androgen blockade leads to outgrowth of androgen independent (AI) cells and the development of castration resistant prostate cancer (CRPC). The transition to androgen independence can occur through several adaptive mechanisms and usually results in the acquisition of a more aggressive phenotype, compared to their androgen sensitive progenitors. However, methods are needed for accurate and early diagnose of these aggressive tumors so appropriate treatments can be selected.

SUMMARY

Methods are disclosed to distinguish aggressive epithelial tumors in a tissue biopsy from, for example, normal, hyperplastic, and benign neoplastic tumors. The methods can also identify epithelial tumors that have become resistant to hormone therapy. Therefore, methods are disclosed for providing diagnosis and prognosis of a subject having, or suspected of having, an epithelial tumor, such as a prostate tumor.

For example, a method is provided for diagnosing an epithelial tumor in a subject that involves assaying a biopsy sample comprising basal cells and luminal cells from the subject for FGD1-related F-actin binding protein (Frabin/FGD4) protein expression, FGD4 gene expression, or a combination thereof. In these embodiments, selective expression of Frabin or FGD4 in the basal cells can be an indication of non-neoplastic cells (normal prostate and BPH), and selective expression of Frabin or FGD4 in the luminal cells can be an indication of a neoplasm.

In some embodiments, the epithelial tumor is a prostate tumor. In these embodiments, selective expression of Frabin protein in the basal cells can be an indication of benign prostate hyperplasia (BPH). In some embodiments, expression of Frabin in both the luminal cells and the basal cells is an indication of prostatatic intraepithelial neoplasia (PIN). In some embodiments, selective expression of Frabin in luminal cells only with concomitant absence of basal cells is an indication of prostate cancer.

In other embodiments, the epithelial tumor is a breast tumor, salivary gland tumor, or a biliary epithelial tumor.

In each of the above embodiments, the method can further involve treating the subject for cancer, e.g., if selective expression of Frabin in the luminal cells is detected. For example, in embodiments where the epithelial tumor is a prostate tumor, treatment can involve radical prostatectomy, radiation therapy, chemotherapy, high-intensity focused ultrasound (HIFU), cryosurgery, hormonal therapy, or a combination thereof.

Also disclosed is a method for providing a prognosis of a subject with an epithelial tumor that involves assaying a biopsy sample from the tumor for the level of Frabin/FGD4 protein, FGD4 gene expression, or a combination thereof, and comparing the level to control values. In these embodiments, an elevated level of Frabin or FGD4 in the luminal cells with concomitant absence of basal cells can be an indication of a poor prognosis.

For example, in embodiments involving a prostate tumor, an elevated level of Frabin or FGD4 in the cancer can be an indication of androgen independent prostate cancer. Frabin expression can be used as a predictive marker for androgen independent prostate cancer although its expression is progressively increased in metastatic and androgen independent prostate tumors. In these embodiments, the method can further involve terminating primary hormonal therapy in the subject if an elevated level of Frabin or FGD4 in the sample is detected. For example, the primary hormonal therapy can be an antiandrogen, such as Bicalutamide (Casodex®), Flutamide (Drogenil®), or Enzalutamide (Xtandi®).

The method can also involve androgen ablation if an elevated level of Frabin or FGD4 in the cancer is detected.

The method can also involve administering to the subject a chemotherapeutic, an angiogenesis inhibitor, or any combination thereof, if an elevated level of Frabin or FGD4 in the sample is detected. Examples of suitable chemotherapeutics include docetaxel (Taxotere®), paclitaxel (Taxol®), mitoxantrone (Novantrone®), carboplatin (Paraplatin®), and vinorelbine (Navelbine®). An example of a suitable angiogenesis inhibitor includes bevacizumab (Avastin®).

Also disclosed is a method for providing a prognosis of a subject with an epithelial tumor that involves assaying a biopsy sample from the tumor for the level of miR-17-92. In some embodiments, a down regulation of miR-17-92 can be an indication of resistance of tumor cells to chemotherapy. This method can be used alone or in combination with Frabin and/or FGD4 detection.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A shows hierarchical clustering of fold change values between samples. FIG. 1B is a Western blot of FGD4/Frabin expression in treated and untreated LNCaP-104S cells.

FIG. 5A is a map of Frabin 3'-UTR. FIG. 5B is a bar graph showing PC-3 cells co-transfected with Luciferase-3'UTR expression vector and miR-17-92 expression vector and then monitored by luciferase activity. FIG. 5C is a bar graph showing quantification of Frabin expression in PC-3 cells ectopically expressing miR-17-92. FIG. 5D shows representative IFA images of FGD4 expression. (Scale bar=10 μm).

FIG. 6A shows representative images from IHC analysis of Frabin expression in 260 prostate tissues. FIG. 6B is graph showing IHC intensity values of Frabin expression. BPH: n=24, PIN-Lo: n=25, Pin-Hi: n=15, G6: n=34, G7(4+3): n=40, G8-10: n=27, Metastatic: n=1, Androgen Independent: n=20.

FIG. 7A is a bar graph showing PC-3 cell viability assessed by MTS assay for cells ectopically expressing miR-17-92. FIG. 7B shows comparative Annexin-V/7-AAD staining analyzed by flow cytometry, including average values for cell populations. FIGS. 7C and 7D show quantification (FIG. 7C) and representative images (FIG. 7D) of Ki-67 staining. (Scale bar=10 μm).

DETAILED DESCRIPTION

Figure 1A:
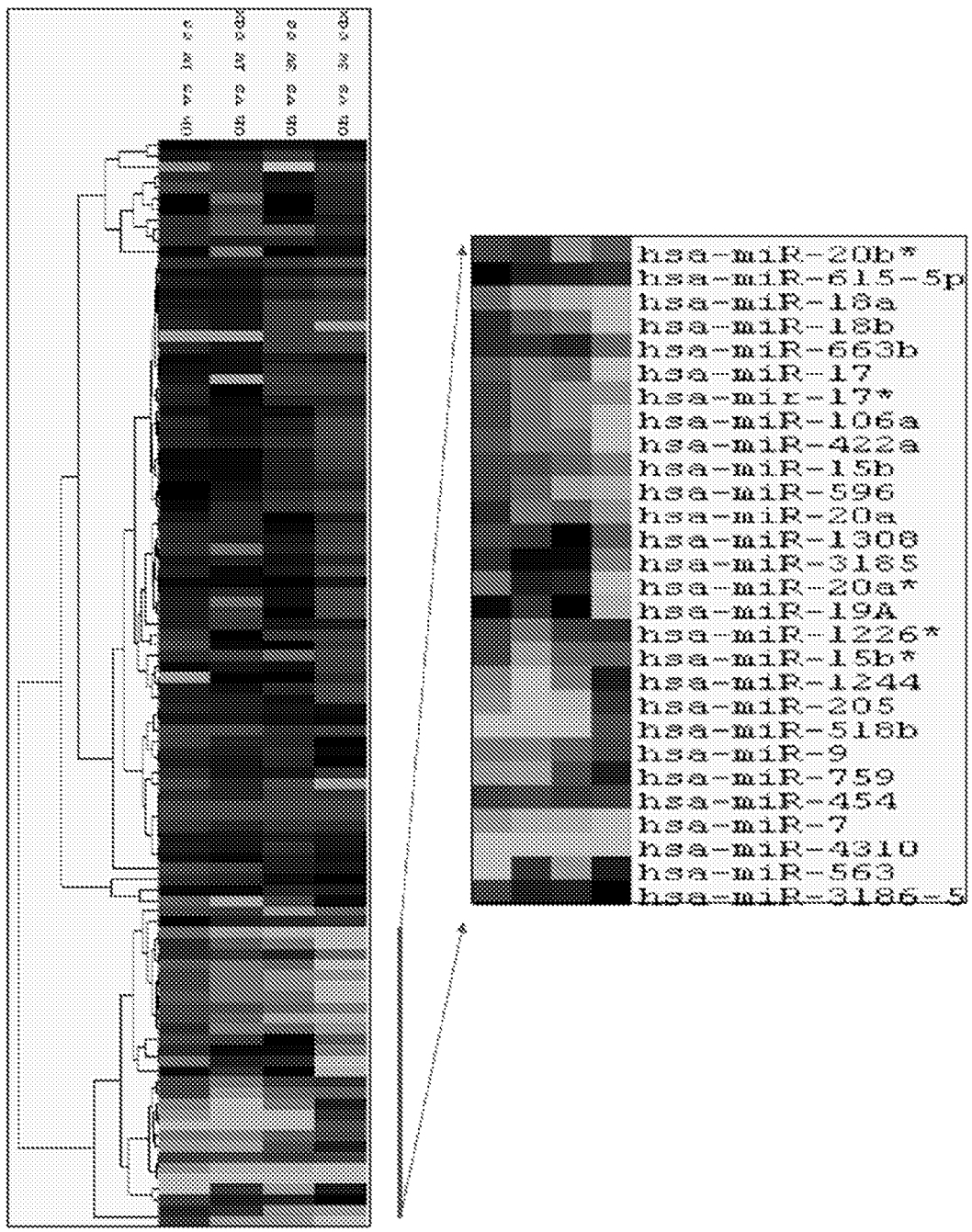
FIGS. 1A and 1B show expression of miR-17-92 and Frabin in Androgen Deprived LNCaP Cells. The androgen dependent cell line, LNCaP-104S, was subjected to androgen deprivation or androgen blockade for 3 weeks. Genome-wide miRNA expression profiling identified the miR-17-92 family to be down regulated by 1 week, and further reduced at 3 weeks of treatment.

Frabin is a guanine exchange factor (GEF) regulator of the Rho family of small GTPases (Rho, Rac, and Cdc42). Rho-GTPases are involved in the regulation of cellular processes dependent on actin cytoskeletal modulation, which includes cell migration, cell morphology, adhesion, and cytokinesis. Rho GTPase activity is dependent on whether GTP or GDP is bound to the protein. Guanine nucleotide exchange factors (GEFs) promote activation of GTPases by causing the dissociation of GDP to allow for the binding of GTP. FGD4/Frabin, has been shown to activate Cdc42 directly and Rac1 indirectly. These cooperative actions of FGD4 and Cdc42/Rac1, result in the formation of filopodia and lamellipodia. However, as disclosed herein, there is an association of Frabin overexpression and development of resistance to anti-androgen drugs or androgen depletion therapy. Frabin is shown to be upregulated in advanced prostate cancer tissues including androgen independent (AI) specimens. There is selective expression of Frabin in basal but not in luminal cells in BPH epithelium, which was absent in PIN and in tumor tissues. Instead, increased Frabin expression was noted in luminal cells in tumor epithelium. Results also showed a significantly higher intensity of expression in androgen independent, and metastatic prostate tissues compared to benign prostatic hyperplasia, and higher scores in tumor tissues compared to BPH tissues. Higher staining intensity in BPH and PIN also correlated with reduced survival time, which suggests that increased Frabin expression is an early event for development of aggressive prostate cancer.

Frabin Detection

In some aspects, Frabin/FGD4 levels and/or location are detected using an immunoassay. Immunoassays, in their most simple and direct sense, are binding assays involving binding between antibodies and antigen. Thus, in some aspects, the method comprises detecting Frabin/FGD4 using an antibody that specifically binds Frabin/FGD4. Antibodies that specifically bind human Frabin/FGD4 are commercially available and can be produced using routine skill.

Many types and formats of immunoassays are known and all are suitable for detecting the disclosed biomarkers. Examples of immunoassays include immunohistochemistry, enzyme linked immunosorbent assays (ELISAs), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP).

Immunoassays can include methods for detecting or quantifying the amount of a molecule of interest (such as the disclosed biomarkers or their antibodies) in a sample, which methods generally involve the detection or quantitation of any immune complexes formed during the binding process. In general, the detection of immunocomplex formation is well known in the art and can be achieved through the application of numerous approaches. These methods are generally based upon the detection of a label or marker, such as any radioactive, fluorescent, biological or enzymatic tags or any other known label.

In some aspects, the method comprises detecting FGD4 gene expression, e.g., using a primer or probe that selectively binds FGD4 mRNA or cDNA. Methods of "determining gene expression levels" include methods that quantify levels of gene transcripts as well as methods that determine whether a gene of interest is expressed at all. A measured expression level may be expressed as any quantitative value, for example, a fold-change in expression, up or down, relative to a control gene or relative to the same gene in another sample, or a log ratio of expression, or any visual representation thereof, such as, for example, a "heat-map" where a color intensity is representative of the amount of gene expression detected. Exemplary methods for detecting the level of expression of a gene include, but are not limited to, Northern blotting, dot or slot blots, reporter gene matrix, nuclease protection. RT-PCR, microarray profiling, differential display, 2D gel electrophoresis, SELDI-TOF, ICAT, enzyme assay, antibody assay, and MNAzyme-based detection methods. Optionally a gene whose level of expression is to be detected may be amplified, for example by methods that may include one or more of: polymerase chain reaction (PCR), strand displacement amplification (SDA), loop-mediated isothermal amplification (LAMP), rolling circle amplification (RCA), transcription-mediated amplification (TMA), self-sustained sequence replication (3SR), nucleic acid sequence based amplification (NASBA), or reverse transcription polymerase chain reaction (RT-PCR).

A number of suitable high throughput formats exist for evaluating expression patterns and profiles. Numerous technological platforms for performing high throughput expression analysis are known. Generally, such methods involve a logical or physical array of either the subject samples, the biomarkers, or both. Common array formats include both liquid and solid phase arrays. For example, assays employing liquid phase arrays, e.g., for hybridization of nucleic acids, binding of antibodies or other receptors to ligand, etc., can be performed in multiwell or microtiter plates. Microtiter plates with 96, 384 or 1536 wells are widely available, and even higher numbers of wells, e.g., 3456 and 9600 can be used. In general, the choice of microtiter plates is determined by the methods and equipment, e.g., robotic handling and loading systems, used for sample preparation and analysis. Exemplary systems include, e.g., xMAP® technology from Luminex (Austin, Tex.), the SECTOR® Imager with MULTI-ARRAY® and MULTI-SPOT® technologies from Meso Scale Discovery (Gaithersburg, Md.), the ORCA™ system from Beckman-Coulter, Inc. (Fullerton, Calif.) and the ZYMATE™ systems from Zymark Corporation (Hopkinton, Mass.), miRCURY LNA™ microRNA Arrays (Exiqon, Woburn, Mass.).

Alternatively, a variety of solid phase arrays can favorably be employed to determine expression patterns. Exemplary formats include membrane or filter arrays (e.g., nitrocellulose, nylon), pin arrays, and bead arrays (e.g., in a liquid "slurry"). Typically, probes corresponding to nucleic acid or protein reagents that specifically interact with (e.g., hybridize to or bind to) an expression product corresponding to a member of the candidate library, are immobilized, for example by direct or indirect cross-linking, to the solid support. Essentially any solid support capable of withstanding the reagents and conditions necessary for performing the particular expression assay can be utilized. For example, functionalized glass, silicon, silicon dioxide, modified silicon, any of a variety of polymers, such as (poly)tetrafluoroethylene, (poly)vinylidenedifluoride, polystyrene, polycarbonate, or combinations thereof can all serve as the substrate for a solid phase array.

In one embodiment, the array is a "chip" composed, e.g., of one of the above-specified materials. Polynucleotide probes, e.g., RNA or DNA, such as cDNA, synthetic oligonucleotides, and the like, or binding proteins such as antibodies or antigen-binding fragments or derivatives thereof, that specifically interact with expression products of individual components of the candidate library are affixed to the chip in a logically ordered manner, i.e., in an array. In addition, any molecule with a specific affinity for either the sense or anti-sense sequence of the marker nucleotide sequence (depending on the design of the sample labeling), can be fixed to the array surface without loss of specific affinity for the marker and can be obtained and produced for array production, for example, proteins that specifically recognize the specific nucleic acid sequence of the marker, ribozymes, peptide nucleic acids (PNA), or other chemicals or molecules with specific affinity.

Microarray expression may be detected by scanning the microarray with a variety of laser or CCD-based scanners, and extracting features with numerous software packages, for example, IMAGENE™ (Biodiscovery), Feature Extraction Software (Agilent), SCANLYZE™ (Stanford Univ., Stanford, Calif.), GENEPIX™ (Axon Instruments).

Definitions

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "sample from a subject" refers to a tissue (e.g., tissue biopsy), organ, cell (including a cell maintained in culture), cell lysate (or lysate fraction), biomolecule derived from a cell or cellular material (e.g. a polypeptide or nucleic acid), or body fluid from a subject. Non-limiting examples of body fluids include blood, urine, plasma, serum, tears, lymph, bile, cerebrospinal fluid, interstitial fluid, aqueous or vitreous humor, colostrum, sputum, amniotic fluid, saliva, anal and vaginal secretions, perspiration, semen, transudate, exudate, and synovial fluid.

The term "hyperplastic cell" refers to a cell undergoing physiological (normal) cell proliferation ("hyperplasia").

The term "neoplastic cell" refers to a cell undergoing abnormal cell proliferation ("neoplasia"). The growth of neoplastic cells exceeds and is not coordinated with that of the normal tissues around it. The growth typically persists in the same excessive manner even after cessation of the stimuli, and typically causes formation of a tumor.

The term "tumor" or "neoplasm" refers to an abnormal mass of tissue containing neoplastic cells. Neoplasms and tumors may be benign, premalignant, or malignant.

The term "cancer" or "malignant neoplasm" refers to a cell that displays uncontrolled growth, invasion upon adjacent tissues, and often metastasis to other locations of the body.

The term "epithelial cancer" refers to any malignant process that has an epithelial origin. Examples of epithelial cancers include, but are not limited to, a gynecological cancer such as endometrial cancer, ovarian cancer, cervical cancer, vulvar cancer, uterine cancer or fallopian tube cancer, breast cancer, prostate cancer, lung cancer, pancreatic cancer, urinary cancer, bladder cancer, head and neck cancer, oral cancer and liver cancer. An epithelial cancer may be at different stages as well as varying degrees of grading. In embodiments, the epithelial cancer is selected from the group consisting of breast cancer, prostate cancer, lung cancer, pancreatic cancer, bladder cancer and ovarian cancer.

A subject suspected of having epithelial cancer includes a subject that presents one or more symptoms indicative of an epithelial cancer (e.g., a noticeable lump or mass) or is being screened for a cancer (e.g., during a routine physical). A subject suspected of having an epithelial cancer may also have one or more risk factors. A subject suspected of having epithelial cancer has generally not been tested for cancer. However, a subject suspected of having epithelial cancer encompasses an individual who has received an initial diagnosis but for whom the stage of cancer is not known and people who once had cancer (e.g., an individual in remission).

The term "metastasis" refers to the spread of malignant tumor cells from one organ or part to another non-adjacent organ or part. Cancer cells can "break away," "leak," or "spill" from a primary tumor, enter lymphatic and blood vessels, circulate through the bloodstream, and settle down to grow within normal tissues elsewhere in the body. When tumor cells metastasize, the new tumor is called a secondary or metastatic cancer or tumor.

The term "aggressive" refers to a cancer that is resistant or insensitive to chemotherapy, has increased malignancy compared to an initial phenotype, and/or has increased metastasis compared to an initial phenotype.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "adjuvant therapy" refers to a treatment used after primary treatments, such as surgery or radiation. Examples of adjuvant therapy include chemotherapy, hormone therapy, radiation therapy, immunotherapy, and targeted therapy. The role of adjuvant therapy is to increase the cure rate of traditional therapies, such as surgery or radiation. By definition, adjuvant therapy is utilized prior to the documentation of persistent disease. That is, it is administered either before (neoadjuvant), concomitant with, or soon after the primary therapeutic strategy, without evidence (such as an elevated PSA level) of recurring disease. The argument for adjuvant therapy is that it extends the therapeutic margin of conventional therapy, which may be achieved by obliterating either microscopic deposits of cancer outside the surgical/radiation field or subclinical metastatic disease.

The term "antibody" refers to natural or synthetic antibodies that selectively bind a target antigen. The term includes polyclonal and monoclonal antibodies. In addition to intact immunoglobulin molecules, also included in the term "antibodies" are fragments or polymers of those immunoglobulin molecules, and human or humanized versions of immunoglobulin molecules that selectively bind the target antigen.

The term "specifically binds", as used herein, when referring to a polypeptide (including antibodies) or receptor, refers to a binding reaction which is determinative of the presence of the protein or polypeptide or receptor in a heterogeneous population of proteins and other biologics. Thus, under designated conditions (e.g. immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ $M^{-1}$ (e.g., $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, and $10^{12}$ $M^{-1}$ or more) with that second molecule.

A number of embodiments of the invention have been described. Nevertheless, it will be understood that various modifications may be made without departing from the spirit and scope of the invention. Accordingly, other embodiments are within the scope of the following claims.

Examples

Example 1: Association of miR-17-92 Family and its Target, Frabin, with Development of Aggressive Prostate Cancer Prolonged androgen blockade leads to outgrowth of androgen independent (AI) cells and the development of castration resistant prostate cancer (CRPC). The transition to androgen independence can occur through several adaptive mechanisms and usually results in the acquisition of a more aggressive phenotype, compared to their androgen sensitive progenitors. Recently, the role of MicroRNAs (miRNAs) has been demonstrated in regulation of gene expression for cancer progression, metastasis, and resistance to therapeutic strategies. However, the role of miRNAs in progression of androgen sensitive prostate cancer to CRPC has not been clearly defined. To study this transition, androgen sensitive (AS) LNCaP prostate cancer cells were subjected to androgen blockade until a subset of cells (CDXR) survived. Genome-wide expression profiling of miRNAs identified a subset of miRNAs that are significantly deregulated in these cells. The miR-17-92 cluster is one of the groups of miRNAs that is down regulated as the cancer cells progresses towards androgen blockade therapy (ADT) resistance.

Results

Figure 2:
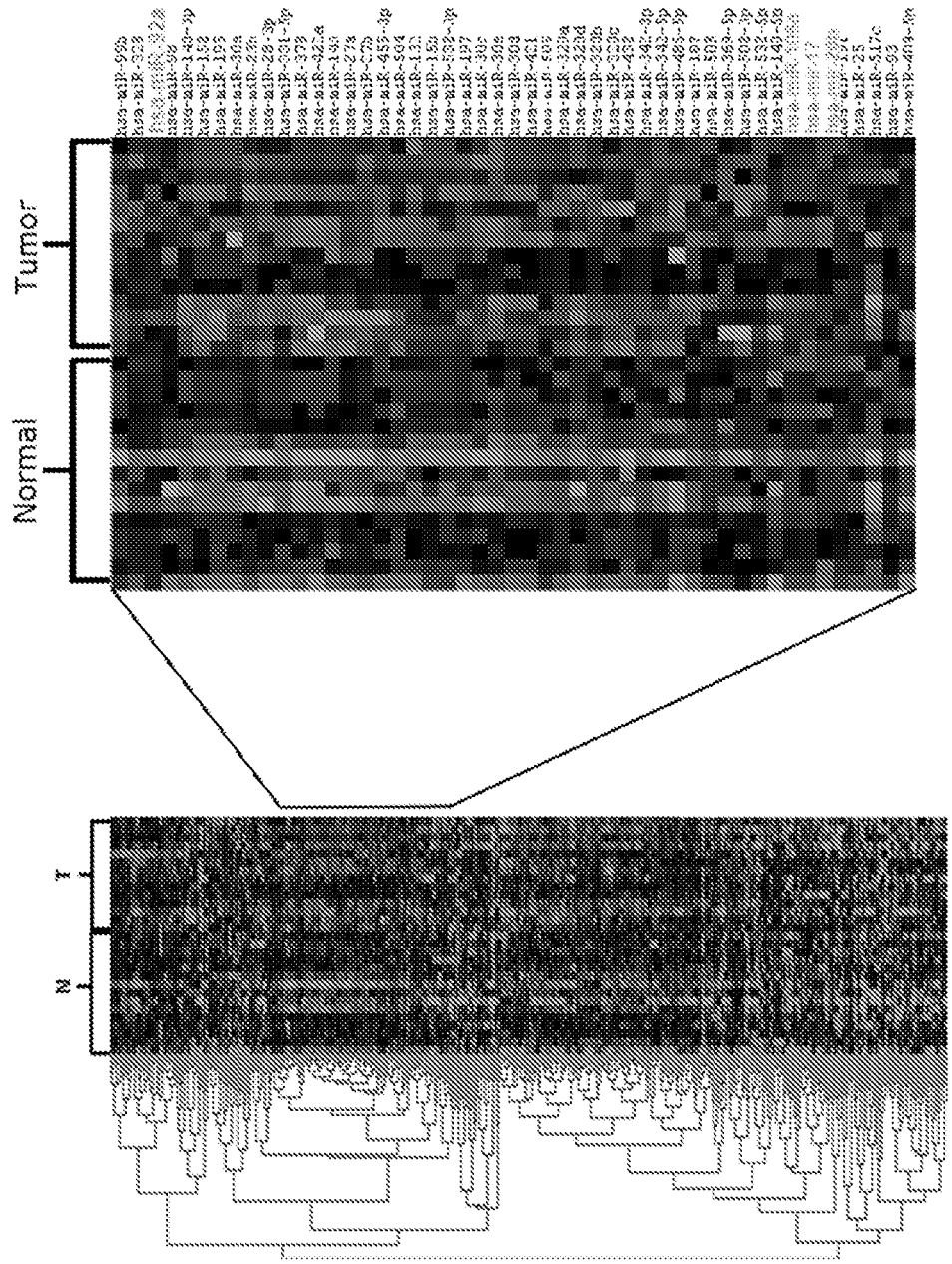
FIG. 2 shows hierarchical clustering of 700 miRNA expression values from paired prostate tumor and uninvolved tissues.
Figure 3A:
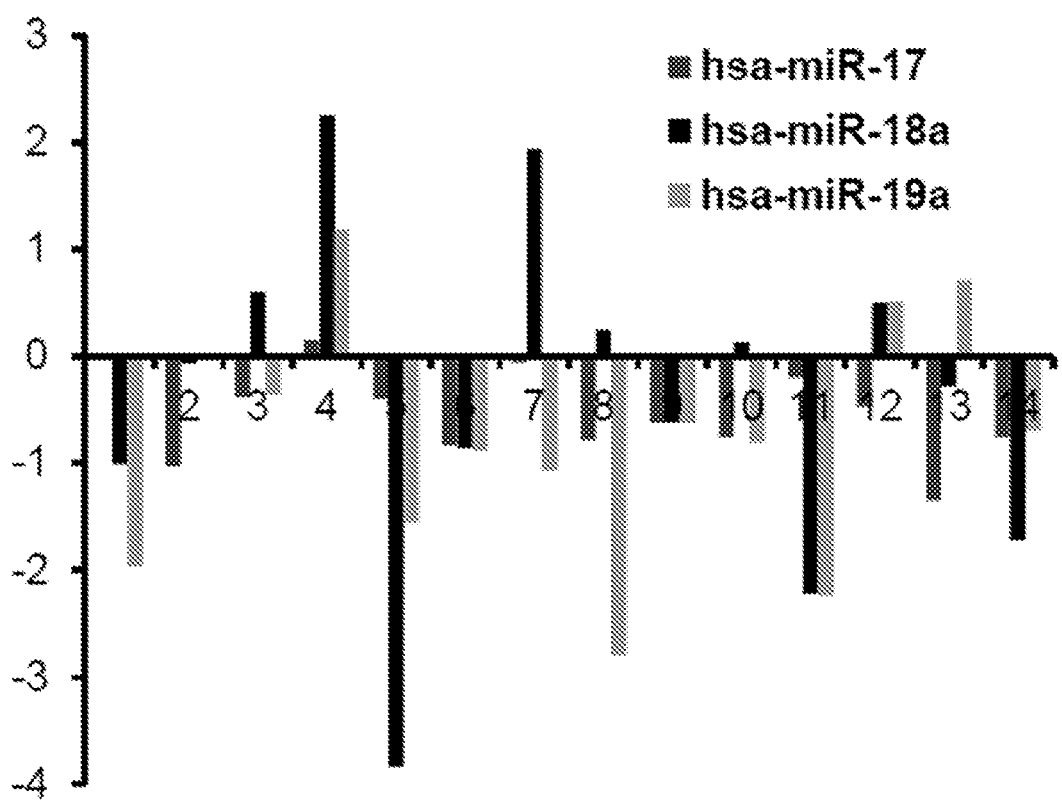
FIGS. 3A and 3B are graphs displaying miR-17-92 family expression fold change values for tumor tissues compared with paired uninvolved tissues, Log2 transformed.
Figure 3B:
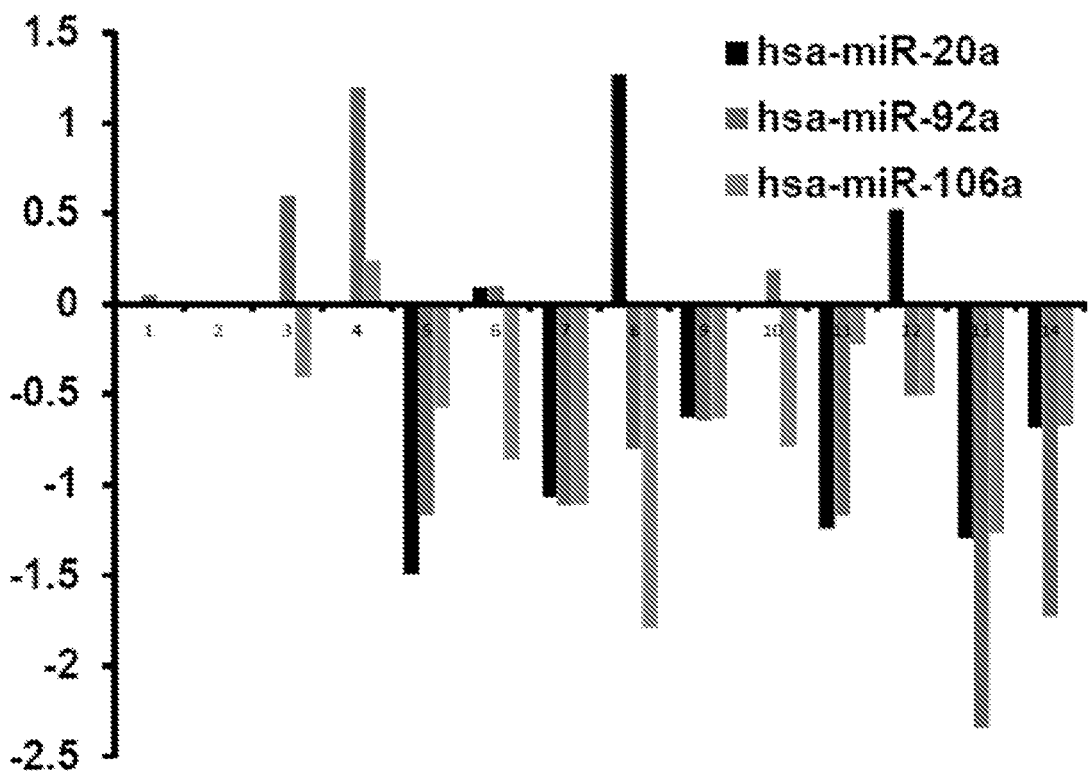
Figure 4:
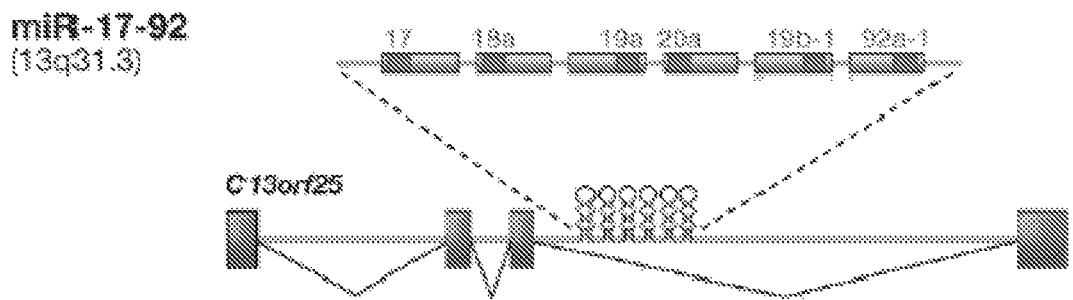
FIG. 4 shows organization of the miR-17-92 gene.

More than a 4-24× down regulation of miRNAs were noted in CDXR cells (Table 1), and patient tumor tissues showed down regulation of these miRNAs in 64-82% of the tissues (FIG. 2).

TABLE 1

Table of fold change in expression values for each sample.

| miRNA ID | 1 wk CSFBS Δ Change | 1 wk CDX Δ Change | 3 wks CSFBS Δ Change | 3 wks CDX Δ Change |
| --- | --- | --- | --- | --- |
| hsa-miR-106a | -2.37 | -3.18 | -5.29 | -9.40 |
| hsa-miR-17 | -2.91 | -3.37 | -2.50 | -24.99 |
| hsa-miR-17* | -3.15 | -3.13 | -5.26 | -3.94 |
| hsa-miR-18a | -2.01 | -4.36 | -14.70 | -14.13 |
| hsa-miR-18b | -1.56 | -2.28 | -4.92 | -21.36 |
| hsa-miR-20a | -2.73 | -3.31 | -3.78 | -4.12 |
| hsa-miR-20a* | -1.78 | -1.25 | -2.64 | -18.17 |
| hsa-miR-20b* | -0.64 | -0.56 | -7.99 | -4.60 |

Figure 5A:
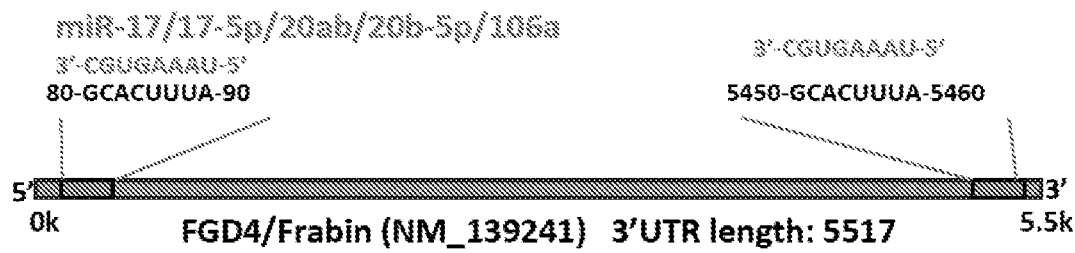
FIGS. 5A to 5D show targeting of Frabin by miR-17-92 miRNAs.
Figure 5B:
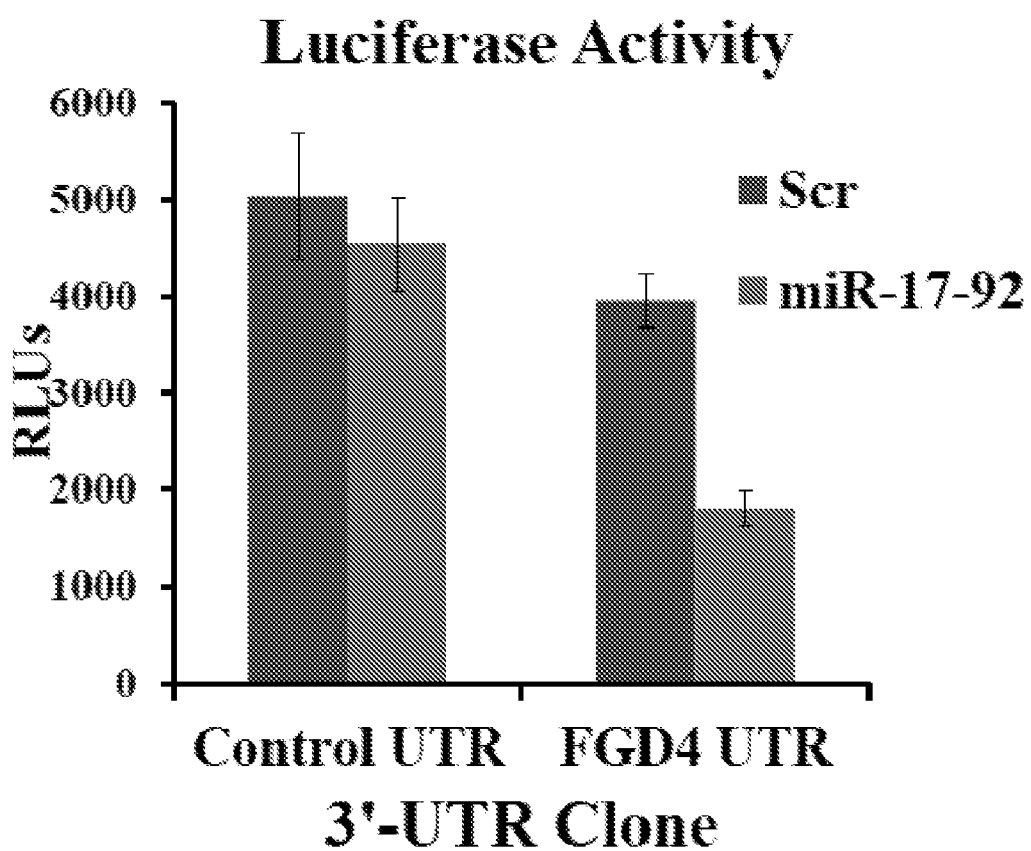
Figure 5C:
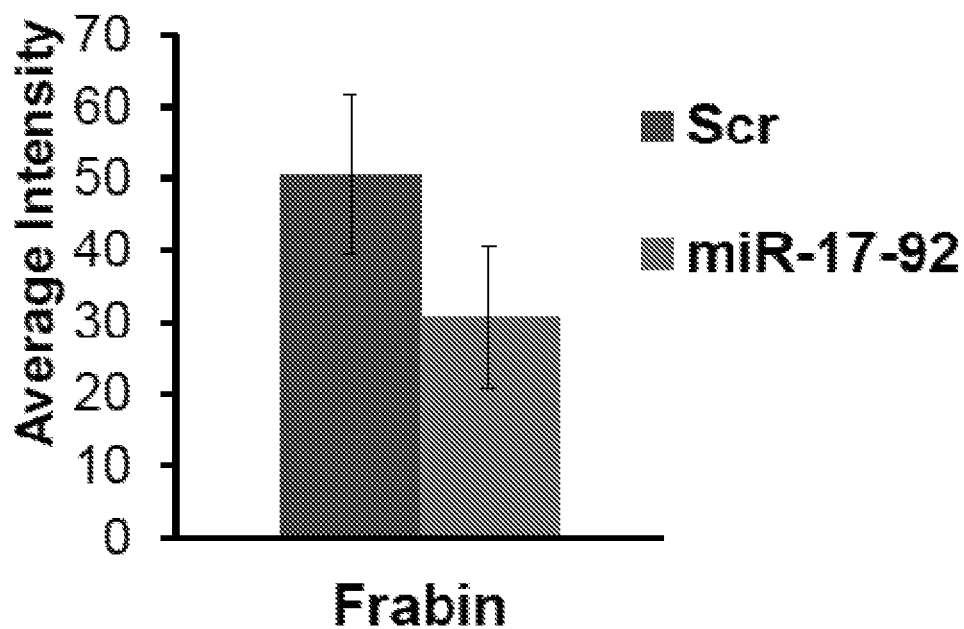
Figure 5D:
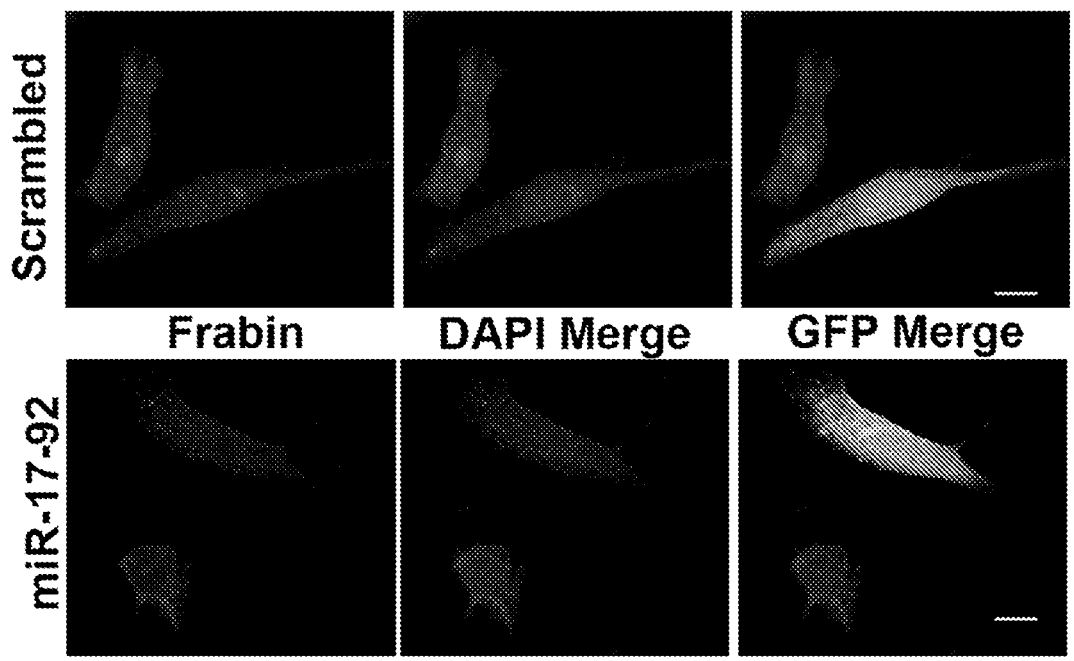

Target prediction database searches identified FGD4/Frabin, a RhoGEF, as one of the targets of this cluster. FIG. 5A is a map of Frabin 3'-UTR. PC-3 cells were co-transfected with Luciferase-3'UTR expression vector and miR-17-92 expression vector, and targeting of Frabin 3'-UTR by miR-17-92 was monitored by luciferase activity (FIG. 5B). Frabin expression was quantified in PC-3 cells ectopically expressing miR-17-92 (FIG. 5C, 5D).

Figure 1B:
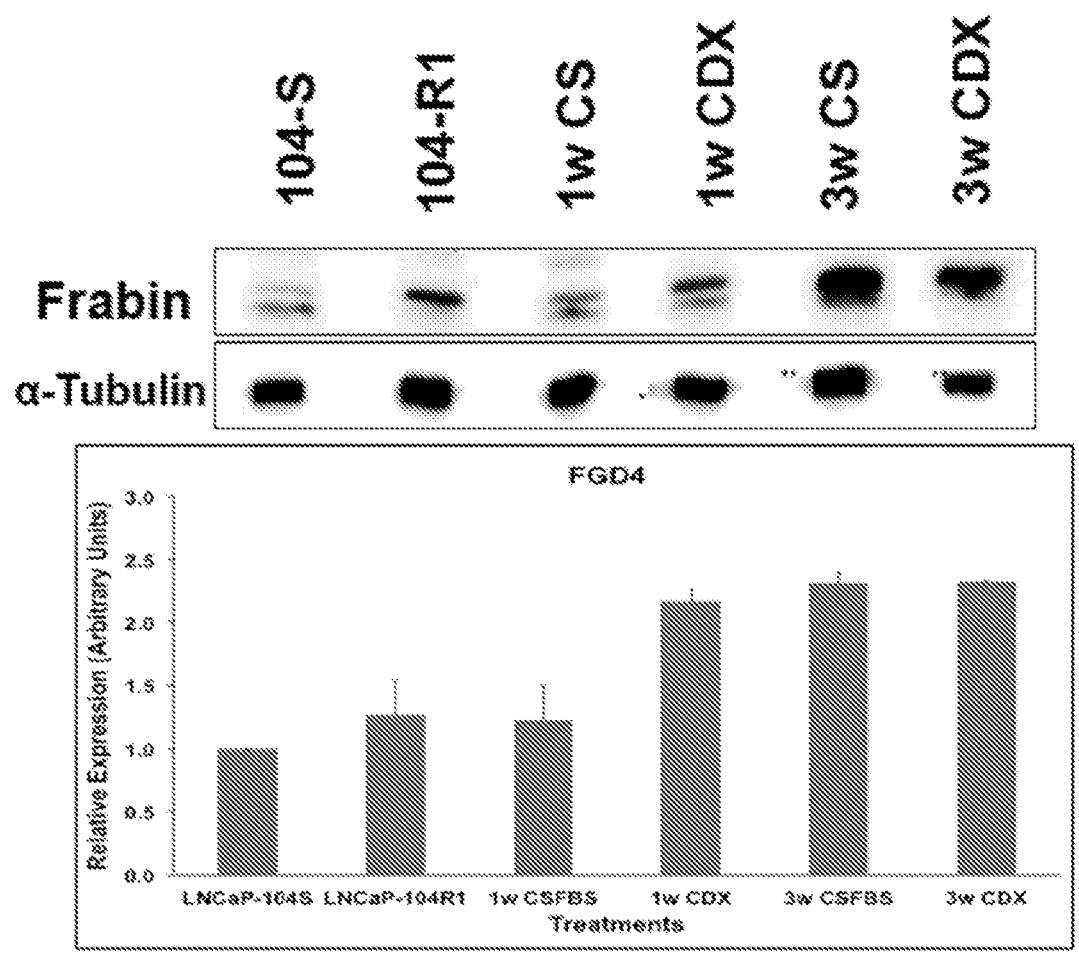
Figure 6A:
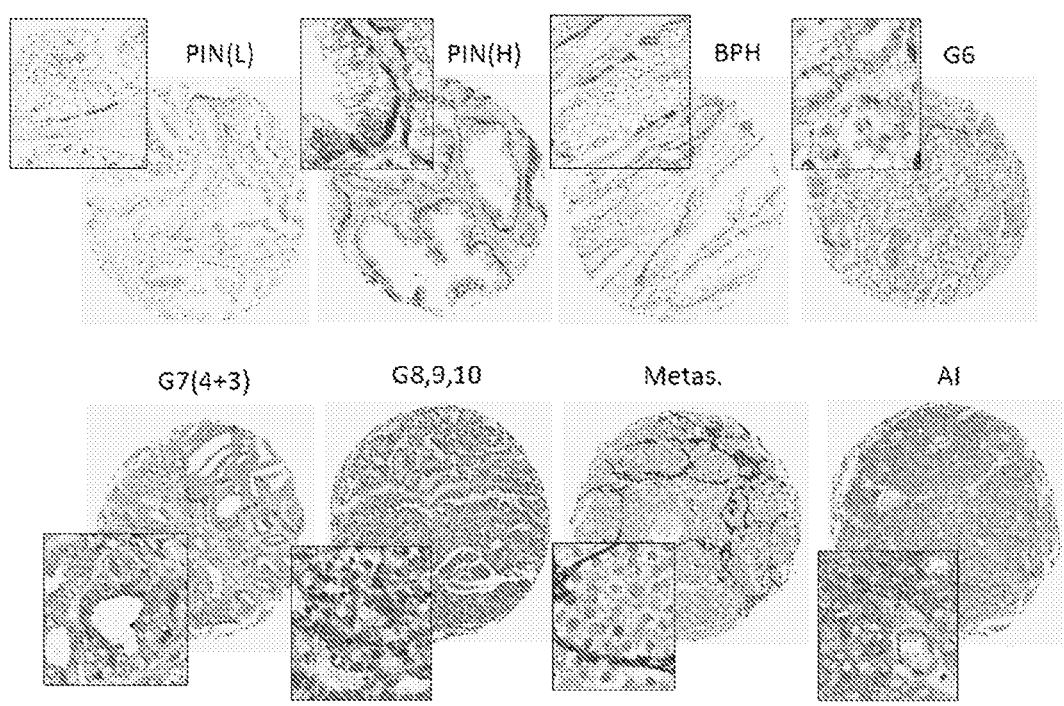
FIGS. 6A and 6B show Frabin expression in prostate tumor TMA.
Figure 6B:
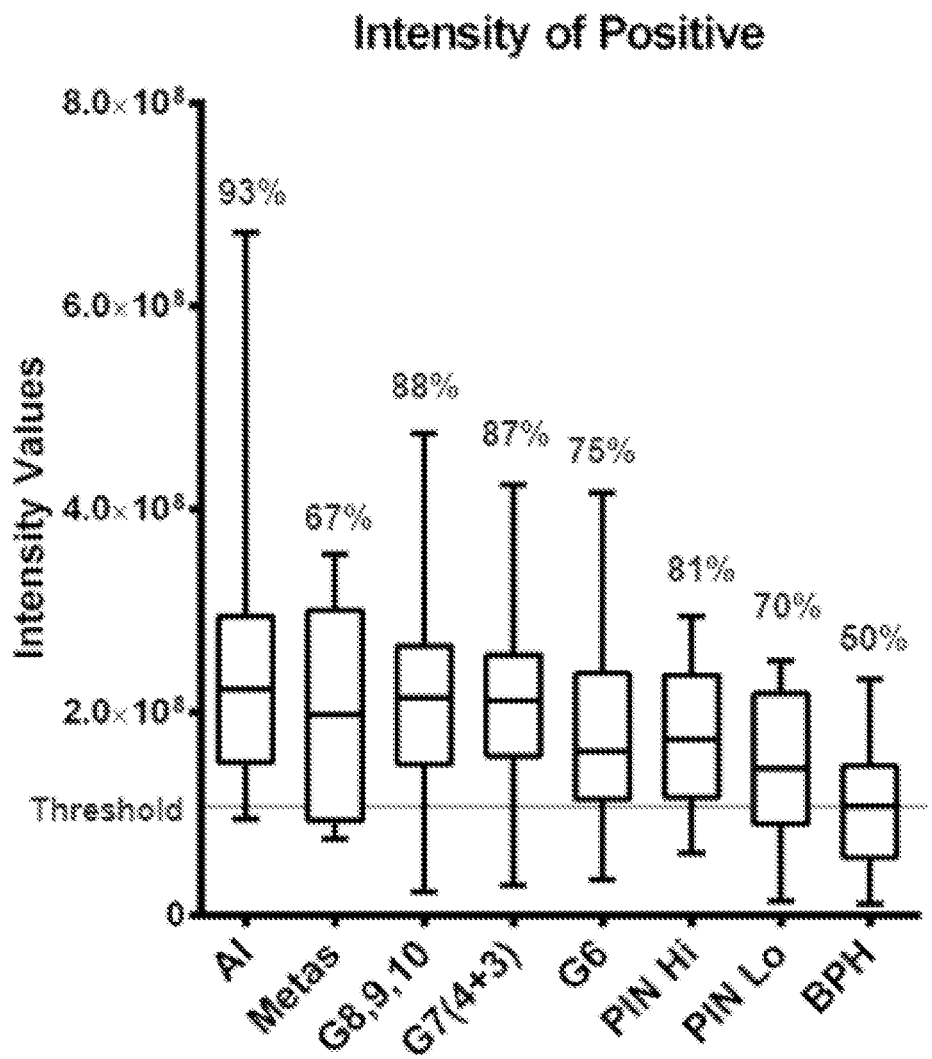
Figure 7A:
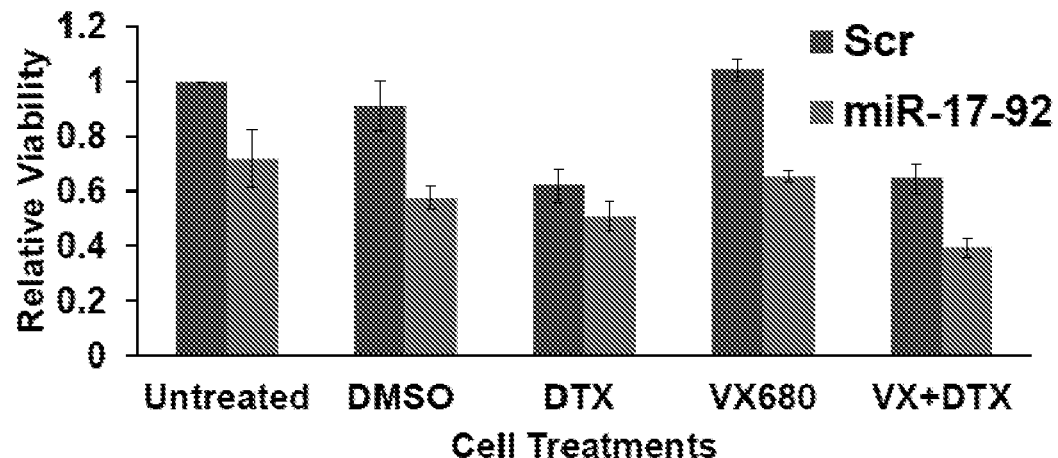
FIGS. 7A to 7D show expression of miR-17-92 reduces viability and proliferation in PC-3 cells.
Figure 7B:
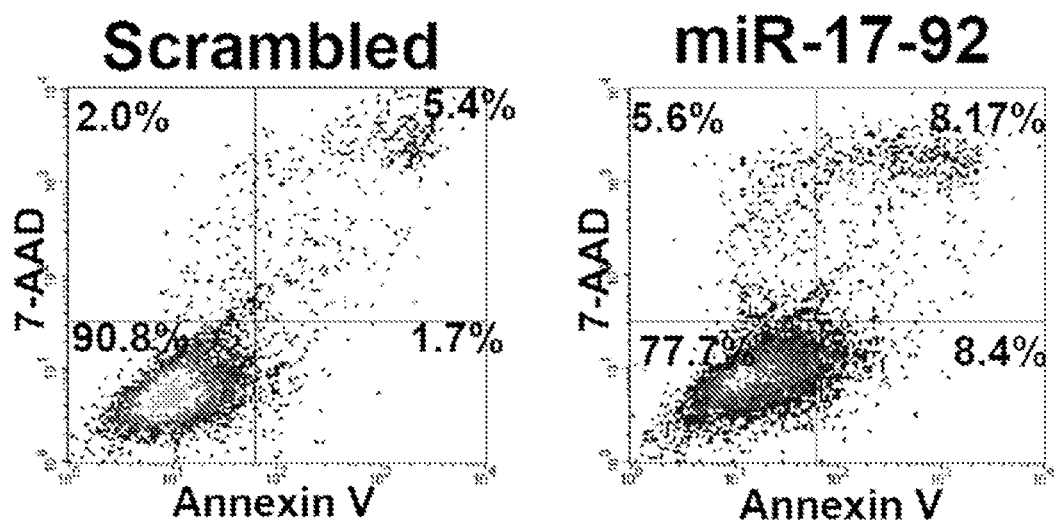
Figure 7C:
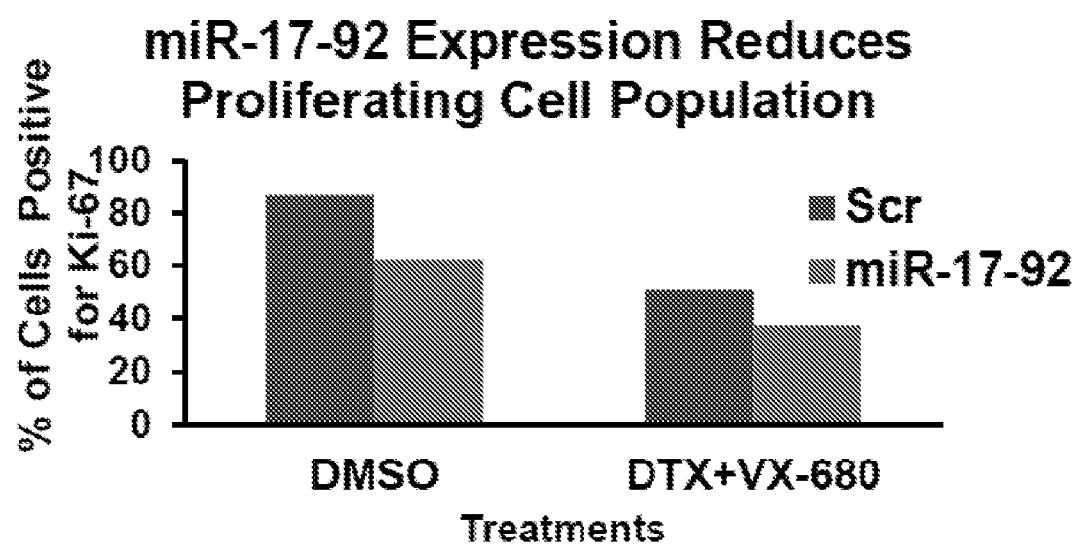
Figure 7D:
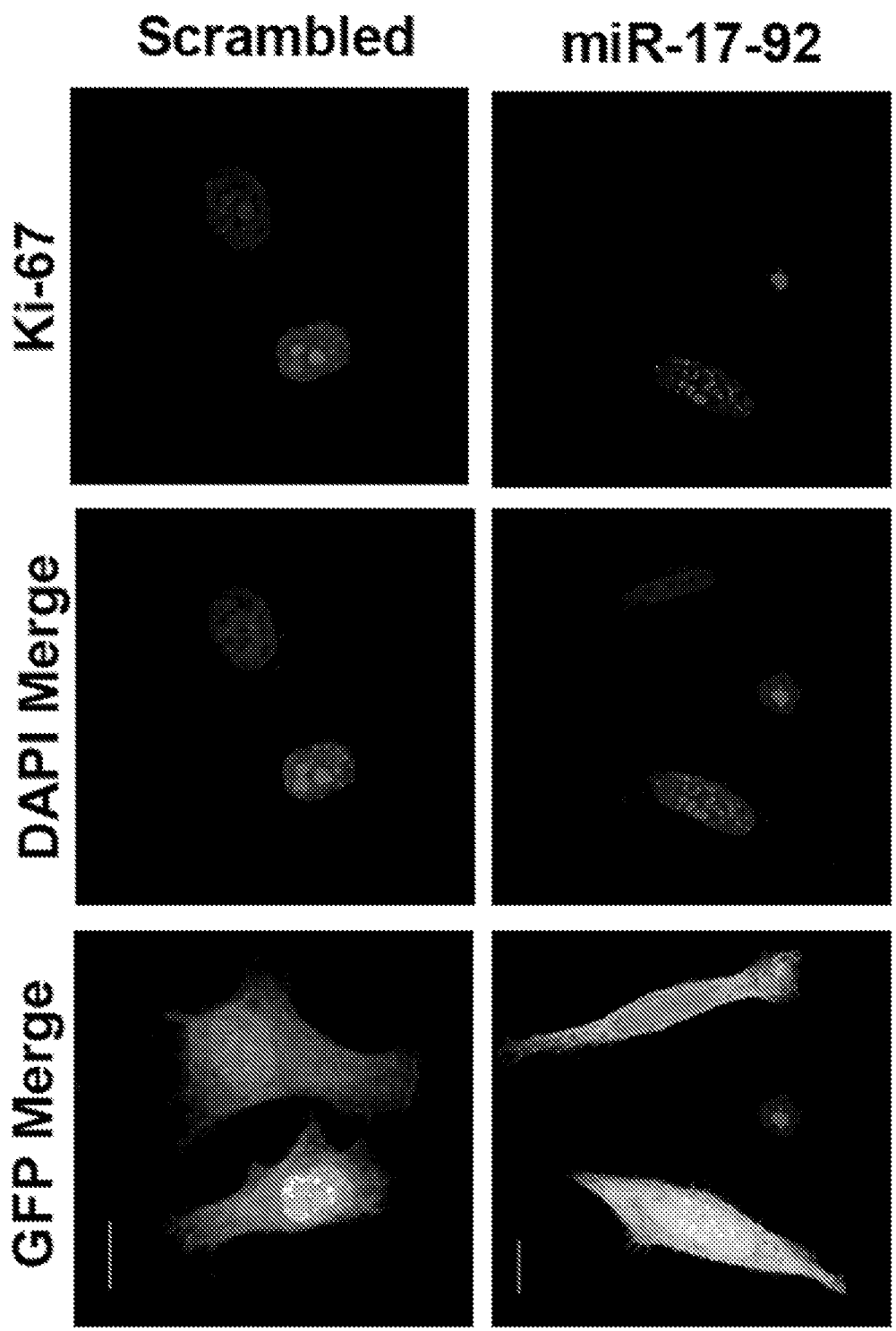

Frabin is involved in filopodia formation and cell migration by interaction with CDC42. Beyond this, little was known about Frabin function in cancer. Western blot analysis of treated cell lysates confirmed increased expression of Frabin in AI and CDXR LNCaP cells (FIG. 1B). Analysis in tissue microarray showed a significant up regulation of Frabin in advanced prostate cancer tissues including AI specimens (FIGS. 6A and 6B). More than 90% of the AI tissues and 88% of tissues with 8-10 Gleason scores showed a median staining intensity between 2-3× higher than BPH tissues.

Ectopic expression of mir-17-92 clusters in AI PC3 cells down regulated Frabin expression and improved sensitivity of these cells to docetaxel (DTX) treatments (FIGS. 7A-7D). Results show involvement of a miRNA cluster/mRNA axis in development of AI and aggressive prostate cancer. This study also provides important insight into the molecular mechanism of development of CRPC and identifies biomarkers and therapeutic targets for management of advanced PCa.

Figure 8A:
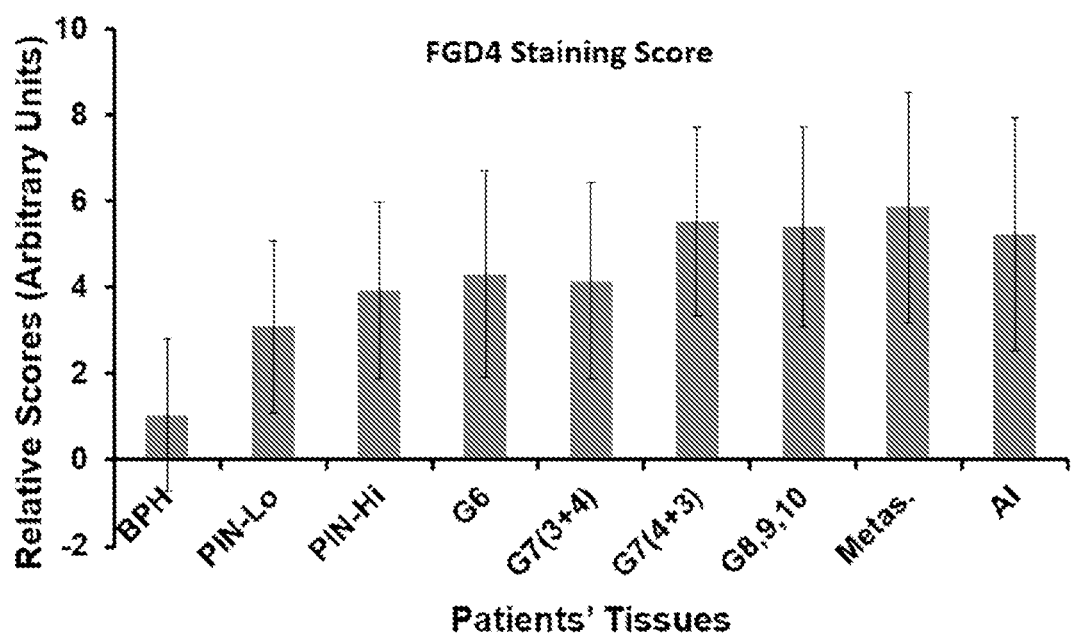
FIGS. 8A and 8B show FGD4 staining (relative scores) as a function of prostate cancer stage.
Figure 8B:
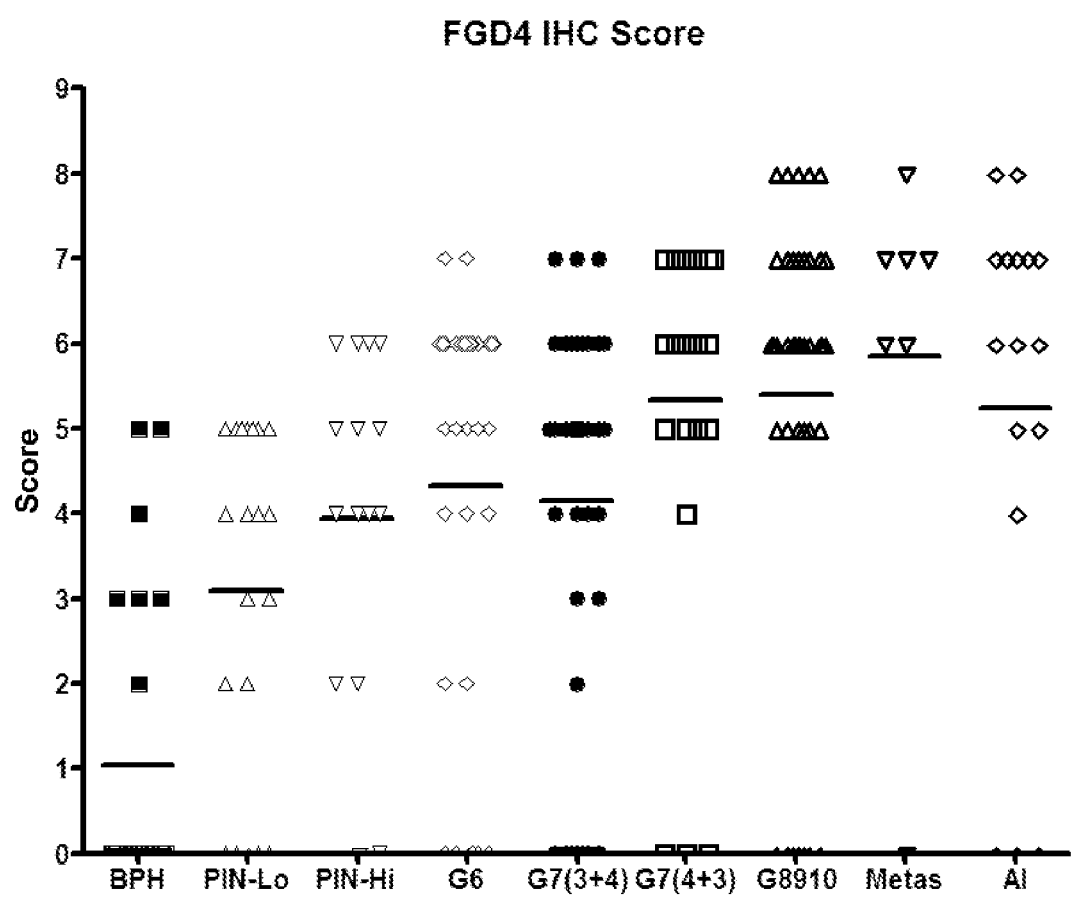
Figure 9A:
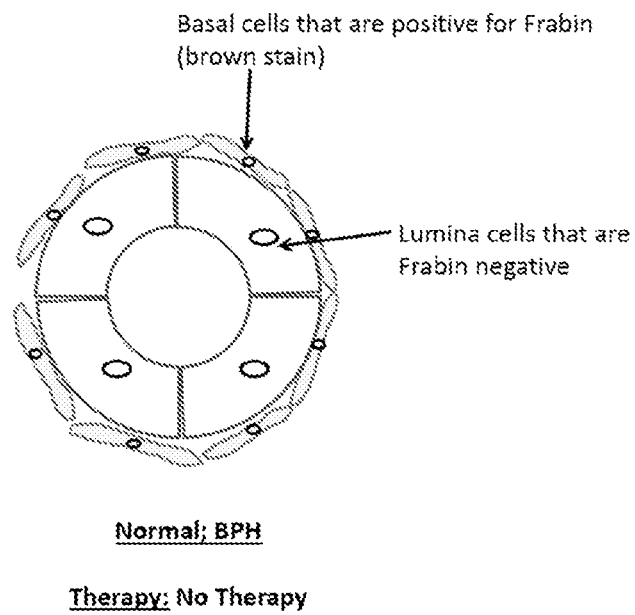
FIGS. 9A to 9C show example diagnostic implications of Fabrin expression in basal and luminal cells.
Figure 9B:
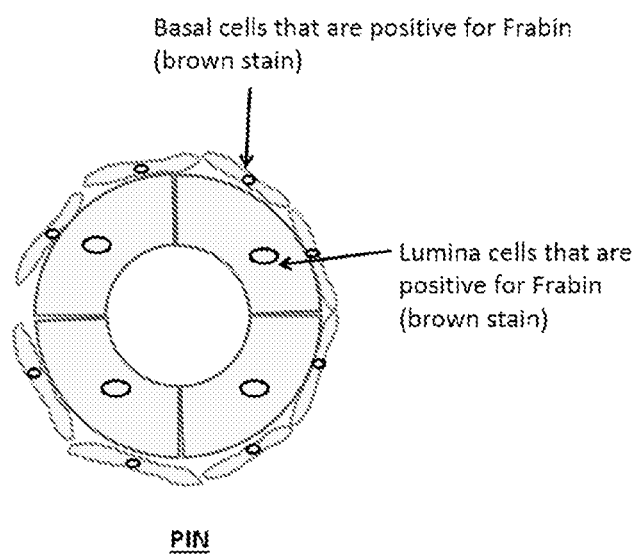
Figure 9C:
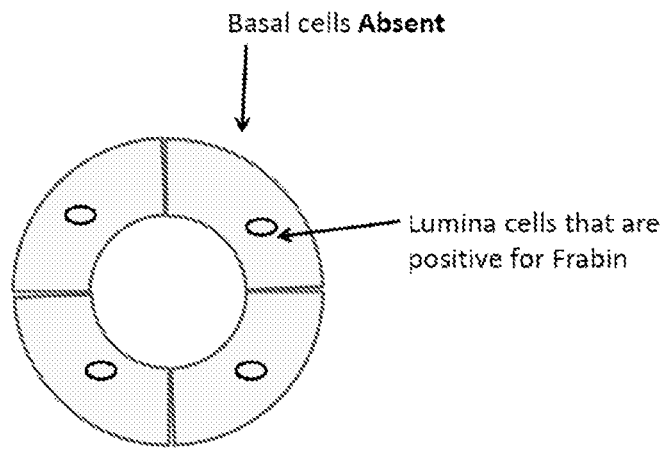

FIGS. 8A and 8B show FGD4 staining (relative scores) as a function of prostate cancer stage.

In summary, the miR-17-92 family is down regulated in LNCaP cells subjected to ADT; the miR-17-92 family down is regulated in 60%+of prostate tumor tissues; the miR-17-92 family directly target expression of Frabin/FGD4; increased Frabin expression associated with advanced PCa; and expression of miR-17-92 family reduces PC-3 cell viability and proliferation.

Figure 10:
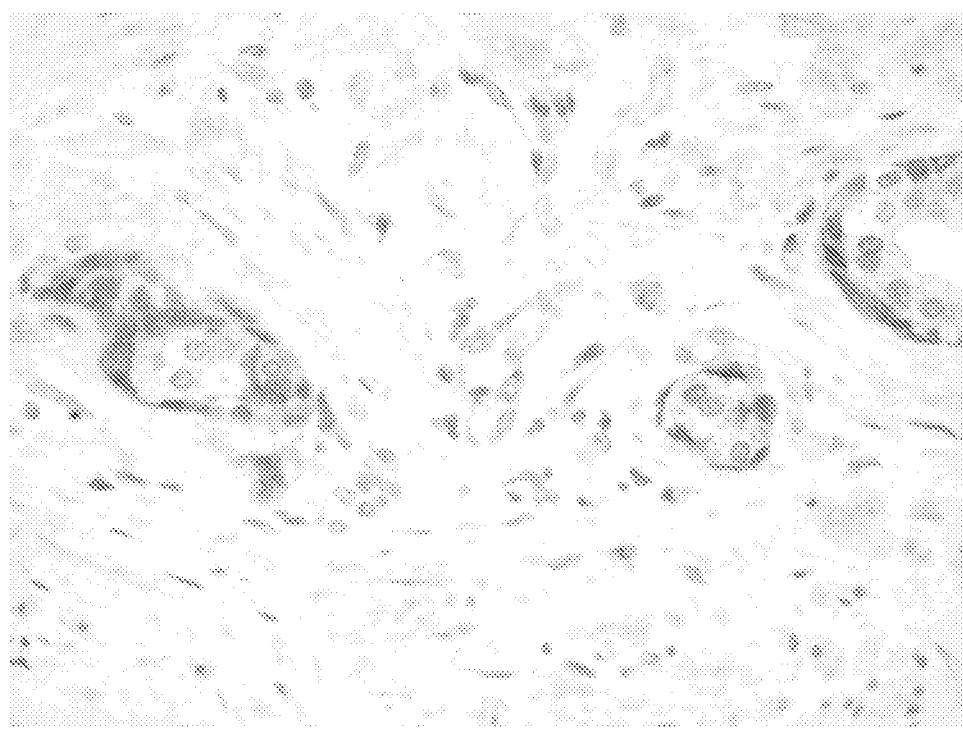
FIG. 10 is an immunohistochemistry image of atrophic prostatic acini showing Frabin positive basal cells.
Figure 11:
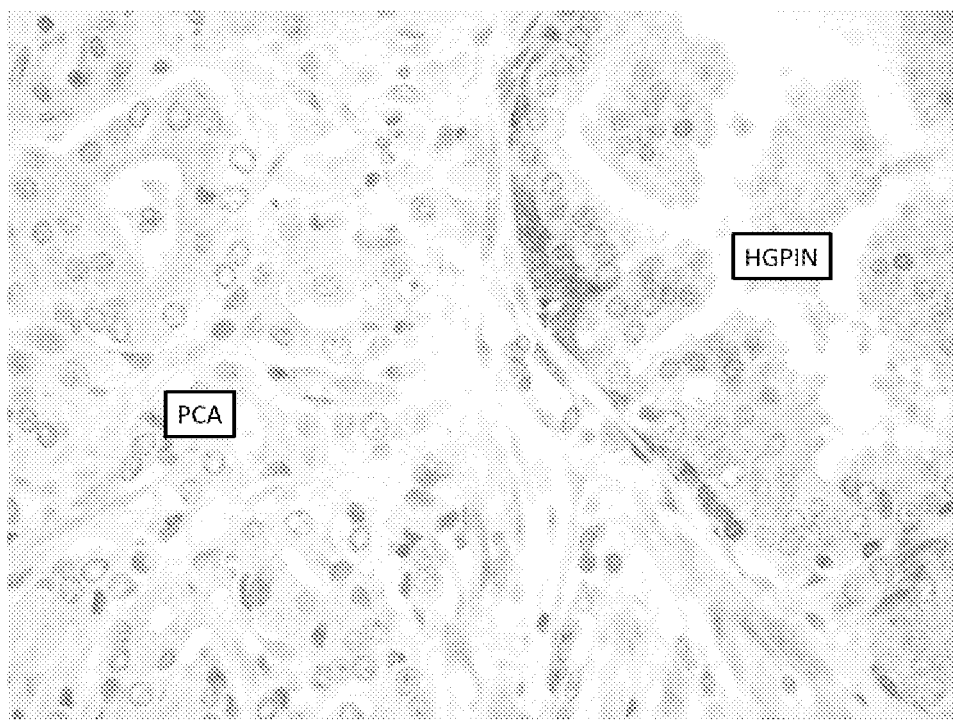
FIG. 11 is an immunohistochemistry image showing the transition between High grade PIN and adjacent prostatic adenocarcinoma (PCA). HGPIN and Frabin decorate the basal cells, which are missing in PCA.
Figure 12:
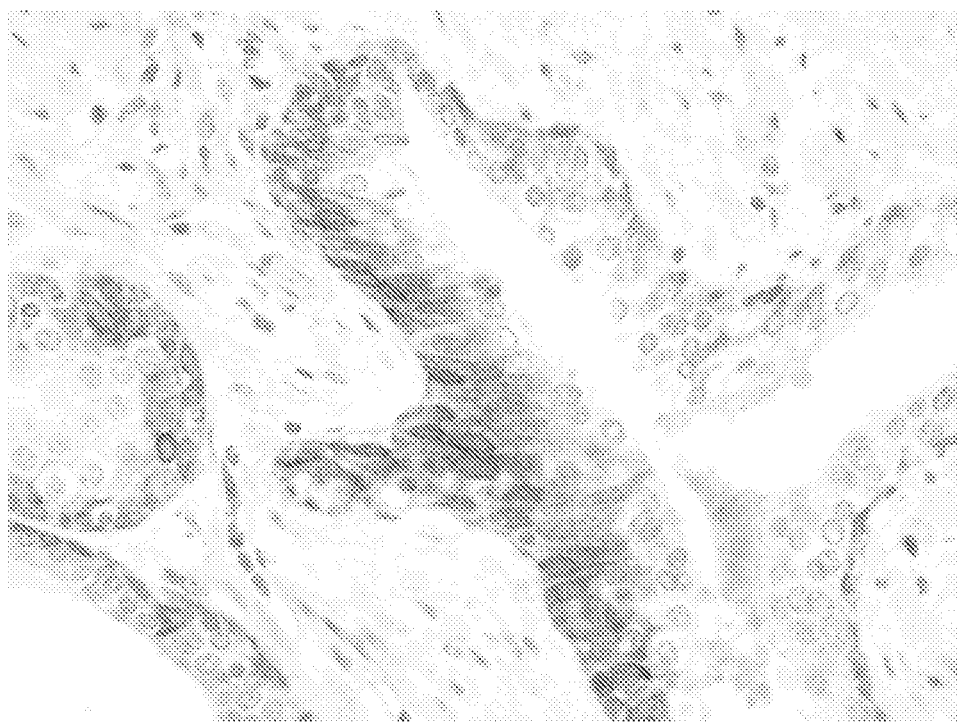
FIG. 12 is an immunohistochemistry image showing Frabin positive basal cell hyperplasia.
Figure 13:
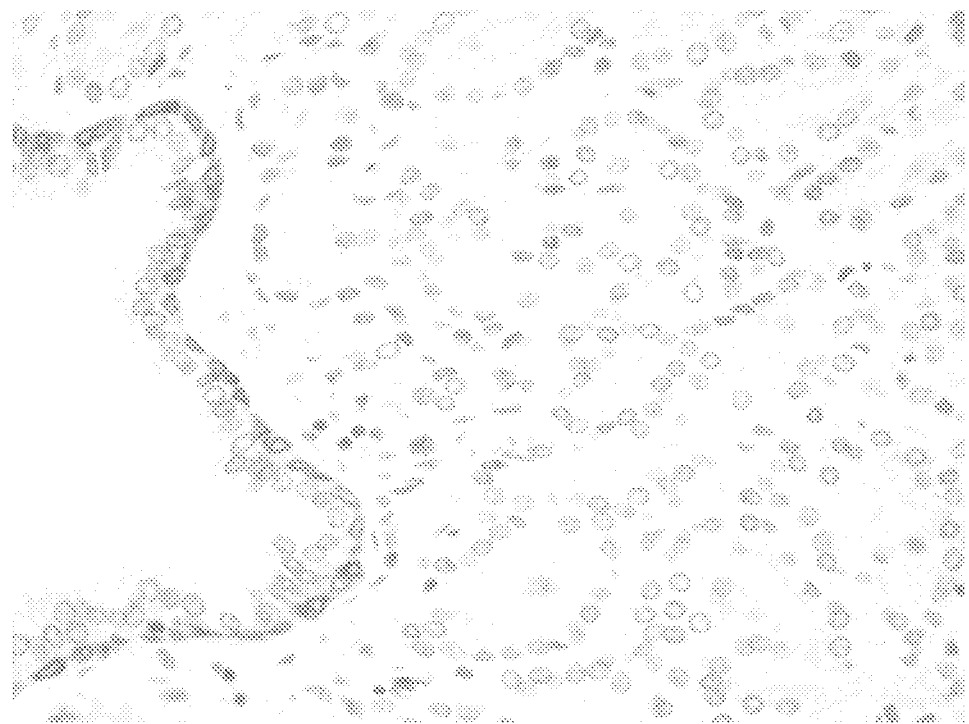
FIG. 13 is an immunohistochemistry image showing an atrophic prostate gland surrounded by a Frabin negative prostate carcinoma. The atrophic gland shows a rim of basal cells staining strongly with Frabin.
Figure 14:
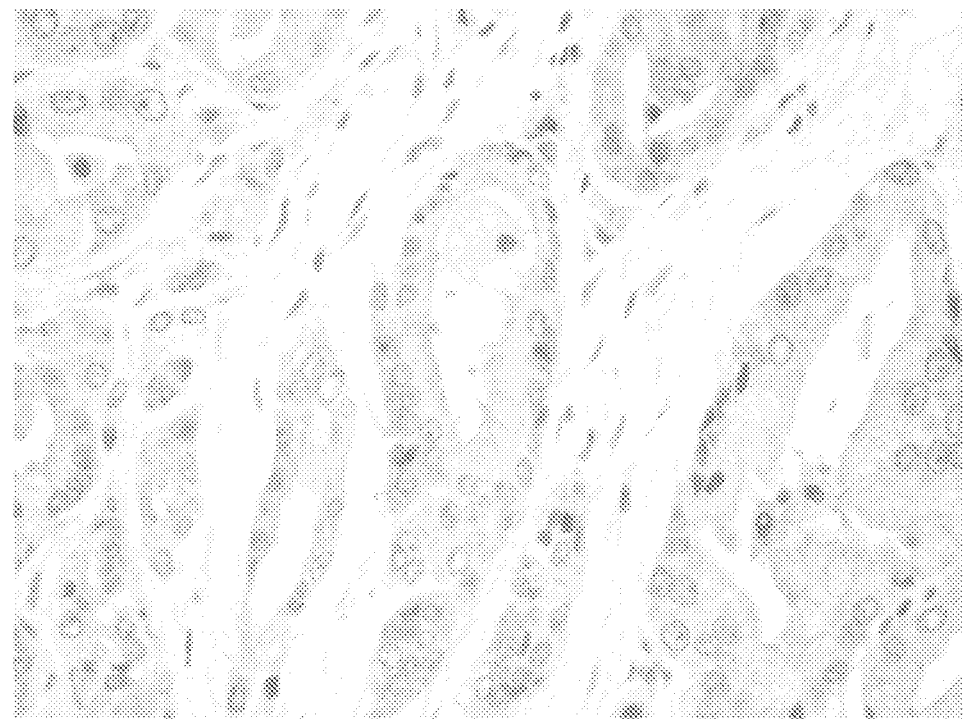
FIG. 14 is an immunohistochemistry image showing a prostate carcinoma showing weak cytoplasmic staining with Frabin, but avoided of basal cells.

FIG. 10 is an immunohistochemistry image of atrophic prostatic acini showing Frabin positive basal cells. FIG. 11 is an immunohistochemistry image showing the transition between High grade PIN and adjacent prostatic adenocarcinoma (PCA). HGPIN and Frabin decorate the basal cells, which are missing in PCA. FIG. 12 is an immunohistochemistry image showing Frabin positive basal cell hyperplasia. FIG. 13 is an immunohistochemistry image showing an atrophic prostate gland surrounded by a Frabin negative prostate carcinoma. The atrophic gland shows a rim of basal cells staining strongly with Frabin. FIG. 14 is an immunohistochemistry image showing a prostate carcinoma showing weak cytoplasmic staining with Frabin, but avoided of basal cells.

Figure 15A:
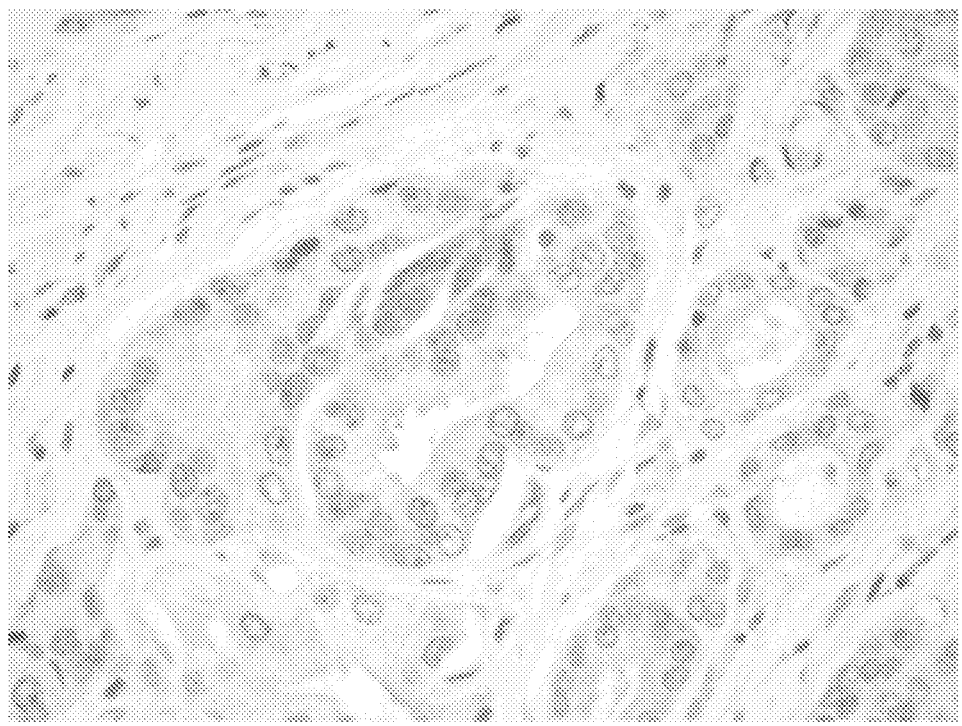
FIGS. 15A and 15B are immunohistochemistry images showing Frabin staining of nerves within prostate cancer.
Figure 15B:
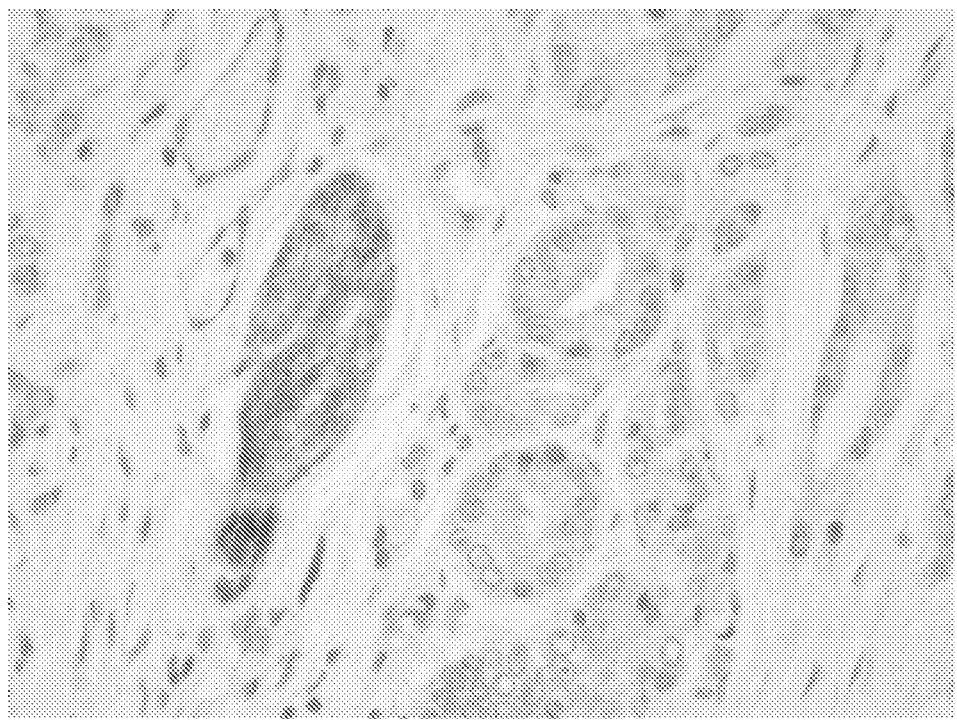

Frabin antibody did also stain segments of nerves within the sections of prostate cancer (FIGS. 15A and 15B). This will facilitate the identification of perineural invasion by prostate cancer. This finding has clinical implication and requires time consuming evaluation of the slides. The antibody will facilitate the identification of nerve involvement. Importantly, the PIN stain does not identify nerves.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for providing a prognosis of a subject with prostate cancer and treating a subject with a poor prognosis, comprising assaying a biopsy sample comprising basal cells and optimally comprising luminal cells from the subject for the level of FGD1-related F-actin binding protein (Frabin/FGD4) protein, FGD4 gene expression, or a combination thereof, and comparing the level to control values, wherein an elevated level of Frabin or FGD4 in the luminal cells and a concomitant absence of Frabin or FGD4 in basal cells is an indication of a poor prognosis; and further treating said subject with an elevated level of Frabin or FGD4 by administering to the subject a chemotherapeutic.

2. The method of claim 1, wherein an elevated level of Frabin or FGD4 in the sample is an indication of androgen independent prostate cancer.

3. The method of claim 1, further comprising androgen ablation if an evaluated level of Frabin or FGD4 in the cancer is detected.

4. The method of claim 1, wherein the chemotherapeutic is selected from the group consisting of docetaxel (Taxotere®), paclitaxel (Taxol®), mitoxantrone (Novantrone®), carboplatin (Paraplatin®), and vinorelbine (Navelbine®).

5. The method of any one of claims 3 or 4, further comprising administering to the subject an angiogenesis inhibitor if an elevated level of Frabin or FGD4 in the sample is detected.

6. The method of claim 5, wherein the angiogenesis inhibitor comprises bevacizumab (Avastin®).

7. A method for providing a prognosis of a subject with prostate cancer who is receiving primary hormonal therapy and treating a subject who has been given a poor prognosis accordingly, comprising assaying a biopsy sample comprising basal cells and optimally comprising luminal cells from the subject for the level of FGD1-related F-actin binding protein (Frabin/FGD4) protein, FGD4 gene expression, or a combination thereof, and comparing the level to control values, wherein an elevated level of Frabin or FGD4 in the luminal cells and a concomitant absence of Frabin or FGD4 in basal cells is an indication of a poor prognosis; and terminating primary hormonal therapy when the subject has an elevated level of Frabin or FGD4 in the sample.

8. The method of claim 7, wherein the primary hormonal therapy is an antiandrogen, such as Bicalutamide (Casodex®), Flutamide (Drogenil®), or Enzalutamide (Xtandi®).

* * * * *

UNITED STATES PATENT AND TRADEMARK OFFICE
CERTIFICATE OF CORRECTION

PATENT NO. : 10,655,185 B2
APPLICATION NO. : 15/525787
DATED : May 19, 2020
INVENTOR(S) : Ratna Chakrabarti et al.

It is certified that error appears in the above-identified patent and that said Letters Patent is hereby corrected as shown below:

On the Title Page

Replace item (73) Assignees: H. Lee Moffitt Cancer Center and Research Institute, Inc., Tampa, FL (US); University of Center Florida Research Foundation, Inc., Orlando, FL (US)

With the following:
--(73) Assignees: H. Lee Moffitt Cancer Center and Research Institute, Inc., Tampa, FL (US); University of Central Florida Research Foundation, Inc., Orlando, FL (US)--

Signed and Sealed this
Twenty-fourth Day of November, 2020

Andrei Iancu
*Director of the United States Patent and Trademark Office*